United States Patent [19]

Buhs et al.

[11] Patent Number: 4,849,562
[45] Date of Patent: Jul. 18, 1989

[54] PROCESS FOR PRODUCING ETHYLENE DICHLORIDE

[75] Inventors: Christoph Buhs, Stade, Fed. Rep. of Germany; Eberhard Dreher, Midland, Mich.; Garnet E. McConchie, Stade, Fed. Rep. of Germany

[73] Assignee: The Dow Chemical Company, Midland, Mich.

[21] Appl. No.: 240,463

[22] Filed: Aug. 26, 1988

Related U.S. Application Data

[63] Continuation of Ser. No. 137,540, Dec. 23, 1987.

[30] Foreign Application Priority Data

Jan. 3, 1987 [DE] Fed. Rep. of Germany ....... 3700132

[51] Int. Cl.$^4$ .................... C07C 17/156; C07C 17/38
[52] U.S. Cl. .................................. 570/241; 570/243; 570/244; 570/245; 570/262; 585/315; 585/142
[58] Field of Search ............... 570/241, 243, 244, 245, 570/262; 585/315, 642

[56] References Cited

U.S. PATENT DOCUMENTS 3,184,515  5/1965  Penner et al. .
3,800,001  3/1974  Prescott et al. .
4,347,391  8/1982  Campbell .

FOREIGN PATENT DOCUMENTS 0005655  4/1981  European Pat. Off. .
1483831  8/1977  United Kingdom ............... 570/243
1505912  4/1978  United Kingdom .

OTHER PUBLICATIONS

CA102:168665U.
Ullmanns Enzyklopedie der technischen Chemie, 5th Edition, pp. 266–271.
Kirk–Othermer's Encyclopedia of Chemical Technology, Third Edition, vol. 5, p. 715.

Primary Examiner—Howard T. Mars
Attorney, Agent, or Firm—A. Cooper Ancona

[57] ABSTRACT

The oxychlorination process for producing ethylene dichloride is carried out by reacting ethylene with hydrogen chloride and oxygen in an oxychlorination reactor. Thereby, ethyl chloride and perhaps vinyl chloride are produced as by-products. The effluent from the reactor is at least fractionated into an ethylene dichloride-rich fraction (I) and an ethyl chloride-rich fraction (II) so that fraction (I) contains less than 50 percent of the total weight of ethyl chloride produced in step (a) and the sum of the weight of ethylene dichloride and vinyl chloride in fraction (II) is less than 30 percent of the weight of ethyl chloride in fraction (II). The ethyl chloride-rich fraction (II) is subjected to a cracking reaction in the presence or absence of an inert diluent wherein ethyl chloride is converted into ethylene and hydrogen chloride in the presence of a catalyst. The total weight of ethylene dichloride and vinyl chloride is less than 5 percent, based on the combined weight of ethyl chloride and any inert diluent.

20 Claims, 1 Drawing Sheet

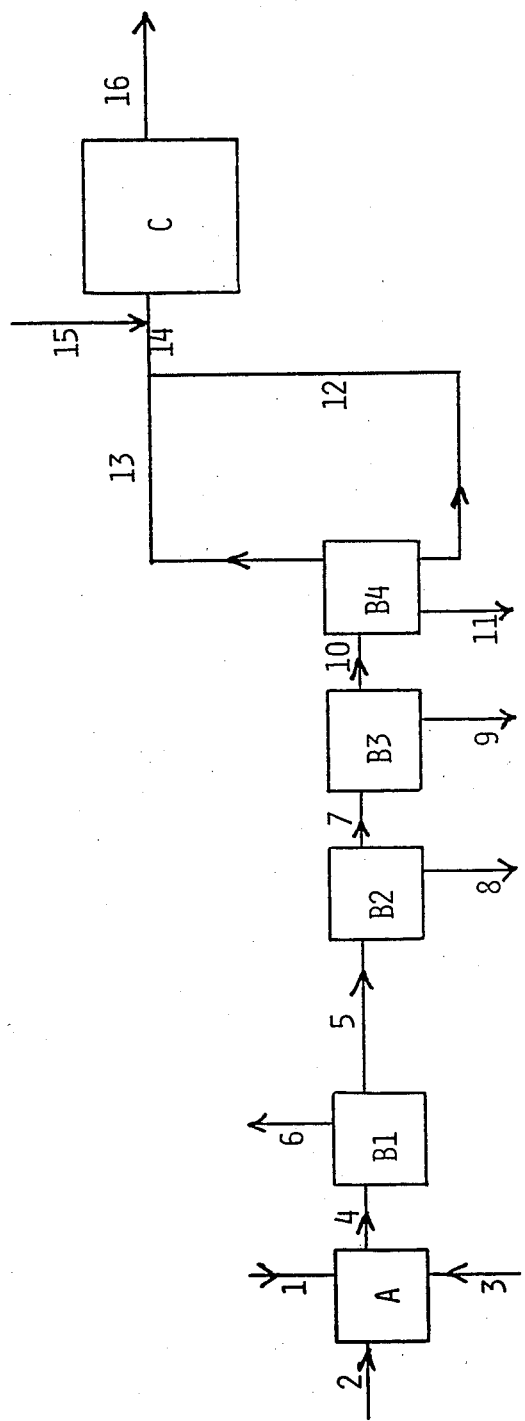

PROCESS FOR PRODUCING ETHYLENE DICHLORIDE

CROSS-REFERENCE TO RELATED APPLICATION

This is a continuation, of application Ser. No. 137,540 filed Dec. 23, 1987.

BACKGROUND OF THE INVENTION

The present invention relates to a process for producing ethylene dichloride. More specifically, it relates to an oxychlorination process in which ethylene is reacted with hydrogen chloride and oxygen in the presence of a catalyst.

1,2-dichloroethane (ethylene dichloride) is used extensively for producing vinyl chloride.

Accordingly, intensive research has been made by those skilled in the art relating to the production of 1,2-dichloroethane. A process which is widely used in industry is the oxychlorination process in which ethylene is reacted with oxygen and hydrogen chloride in the presence of a catalyst such as copper dichloride. Extensive patent literature exists relating to the catalysts in the process and to the process technologies which, among others, try to maximise yield of ethylene dichloride. The by-products from existing processes are usually burnt and hydrogen chloride is recovered. Although the yield of ethylene dichloride is quite high, generally between 90 and 97 percent, depending on the process type and conditions, the incineration of the by-products in large scale production is a problem for the environment.

European Patent No. 0 005 655 suggests oxidative destruction of the by-products using a catalyst containing platinum or iridium on a support of alumina having the eta crystallographic structure to improve the incineration process.

However, incineration of the by-products remains uneconomical and efforts are necessary in order to keep the pollution of the environment to a low level.

In European patent application 0 132 971 an oxychlorination process is disclosed wherein hydrogen chloride gas and oxygen are reacted with an unsaturated organic compound. Chlorine containing organic residues are combusted in an oxygen-rich flame whereby hydrogen chloride is produced which is recycled to the oxychlorination process. However, this process is rather inconvenient because a high combustion temperature of more than 2000° C. is required to ensure complete destruction of the residues. European patent application 0 132 971 discloses that steps must be taken to avoid corrosion of the chamber material in the presence of hydrogen chloride.

In the German Auslegeschrift DE-AS-24 00 417 it is suggested to adsorb the by-products of the oxychlorination process partially on activated carbon and to burn the nonadsorbed by-products such as ethylene at a temperature between 500° C. to 2000° C. The adsorbed impurities such as ethylene dichloride and ethyl chloride are then desorbed with vapour.

However, a careful separation of vapour and chlorinated by-products is required after the desorption step in order to avoid pollution of water.

Accordingly, it would be desirable to overcome these disadvantages of known oxychlorination processes for producing ethylene dichloride.

It has been found that the problem of by-products disposal can be reduced by separating ethylene dichloride and ethyl chloride (which is one of the main by-products in the oxychlorination process) and then converting ethyl chloride to ethylene and hydrogen chloride in the presence of a catalyst.

SUMMARY OF THE INVENTION

The present invention is an oxychlorination process for producing ethylene dichloride by
 (a) reacting ethylene with hydrogen chloride and oxygen in the presence of an oxychlorination catalyst in an oxychlorination reactor, whereby ethyl chloride or both ethyl chloride and vinyl chloride are produced as byproducts
which process is characterised in that it comprises the further steps of
 (b) dividing, in one or more steps, the effluent from the oxychlorination reactor into at least (i) an ethylene dichloride-rich fraction (I) and (ii) an ethyl chloride-rich fraction (II) in such a fashion that fraction (I) contains less than 50 percent of the total weight of ethyl chloride produced in step (a) and the sum of the weight of ethylene dichloride and vinyl chloride in fraction (II) is less than 30 percent of the weight of ethyl chloride in fraction (II) and
 (c) subjecting fraction (II) to a cracking process in the presence or absence of an inert diluent whereby fraction (II) contains less than 5 percent ethylene dichloride and vinyl chloride based on the combined weight of ethyl chloride and inert diluent in fraction (II) prior to cracking, the cracking process is carried out in the presence of a cracking catalyst in a cracking reactor and ethyl chloride is converted into ethylene and hydrogen chloride.

From Kirk-Othmer "Encyclopedia of Chemical Technology" 3rd edition, 1979, vol. 5, page 715, G. M. Schwab and H. Noller, z.Eletrochem. 58, 762 (1954) and A. Heinzelmann et al., J. Monatsh. Chemie 102, 1750 (1971) it is generally known that ethyl chloride is decomposited to ethylene and hydrogen chloride at about 300° C. in the presence of certain cracking catalysts. However, these references do not suggest anywhere to use a cracking step in the oxychlorination process. The skilled artisans have concentrated on incineration methods for disposing of the by-products in the oxychlorination process.

Surprisingly, it has been found that a good conversion rate of ethyl chloride to ethylene can be achieved in the process of the present invention and that unconverted ethylene from the oxychlorination step (a) does not substantially affect the conversion rate in step (c).

The oxychlorination process of the present invention is useful for producing ethylene dichloride on a large scale. The process of the present invention allows a substantial saving of ethylene which is used as raw material but which is expensive. By the present invention the yield of produced ethylene dichloride, based on the amount of ethylene consumed, can be increased by 1 to 2 percent. Depending on the process conditions, even 1.5 to 2 percent yield increase can be achieved.

BRIEF DESCRIPTION OF THE DRAWING

The drawing illustrates a flow sheet of one embodiment of process of the present invention.

DETAILED DESCRIPTION OF THE INVENTION

Process step (a) is well known in the literature. A general description of the oxychlorination reaction is published in ULLMANNS Enzyklopedie der technischen Chemie, 4th Edition, volume 9, pages 428 to 431. A preferred process step (a) is described in U.S. Pat. No. 3,184,515.

Ethylene is reacted with hydrogen chloride and oxygen in the presence of a oxychlorination catalyst. The typical molar ratios of hydrogen chloride:oxygen:ethylene used in industry are from 1.8 to 3 moles, preferably from 1.9 to 2.4 moles hydrogen chloride and from 0.4 to 0.7 moles, preferably from 0.5 to 0.6 moles oxygen per mole ethylene. Ethylene may originate from hydrocarbon cracking facilities and may contain usual impurities such as methane, ethane and other hydrocarbons.

The oxychlorination step (a) may be carried out in liquid phase in which the catalyst is dissolved. In a liquid phase reaction the temperature is preferably from 150° C. to 200° C., more preferably from 170° C. to 190° C. and the pressure is preferably from 13 to 22 bar, more preferably from 15 to 20 bar.

However, a gaseous phase oxychlorination is preferred for the purpose of the present invention. In general, the temperature in the gaseous phase oxychlorination process is from 200° C., preferably from 210° C. and more preferably from 230° C. and up to 450° C., preferably up to 350° C. and more preferably up to 280° C. In general, the pressure is from 1 bar, preferably from 2 bar and more preferably from 3 bar, up to 10 bar, preferably to 8 bar, more preferably to 7 bar.

Useful oxychlorination catalysts for the purpose of the present invention are also known. A preferred catalyst is copper(II) chloride. Copper(II) chloride can be used together with alkali or alkaline earth metal chlorides, for example potassium chloride. The copper chloride catalyst can be deposited on a conventional carrier material such as high surface aluminum oxides, preferably gamma-alumina, silica, celite or zeolites.

Well known reactor types are useful for the purpose of the present invention, such as fixed bed reactors or fluidised bed reactors.

Since the oxychlorination reaction is highly exothermic, efficient temperature control is necessary. In the gas phase reaction, it is preferred to dilute the reactive gases with one or more inert gases such as nitrogen. Dilution may also be achieved by using air as the oxygen source in the oxychlorination process. When using air in a continuous oxychlorination process, excess nitrogen is removed from the reactor in order to avoid a pressure build up. Preferably, the oxychlorination process is carried out by continuously feeding oxygen into the reactor and by diluting it with nitrogen which is continuously recycled into the oxychlorination reactor after the reaction.

The mixture produced in the oxychlorination reactor is removed from the reactor and preferably cooled to a temperature of less than 200° C., more preferably to a temperature between 20° C. and 160° C., preferably at a pressure of from 1 to 10 bar, more preferably from 2 to 8 bar. It is advisable to remove residual amounts of unreacted hydrogen chloride from the mixture produced in the oxychlorination reactor, for example by washing it with hot water, a hot alkaline solution such as aqueous sodium hydroxide or with both. The washing of hydrogen chloride is preferably carried out at a temperature of less than 200° C., more preferably less than 150° C. and a pressure of 1 to 5 bar. The amount of ethyl chloride produced in the oxychlorination step a) depends of course on the reaction conditions. In general, it is between 1 to 3 percent, based on the weight of produced ethylene dichloride.

In process step (b) the effluent from the oxychlorination reactor, from which excess hydrogen chloride preferably has been separated, is divided in one or more steps into at least (i) an ethylene dichloride-rich fraction (I) and (ii) an ethyl chloride-rich fraction (II). Preferred fractionation steps are described in more detail below with respect to the drawing.

In order to reach a substantial process improvement, the ethylene dichloride-rich fraction (I) should contain less than 50 percent, preferably less than 30 percent, more preferably less than 20 percent of the total weight of ethyl chloride which has been produced in step (a). Less efficient fractionation is possible but renders the process uneconomically. At least 50 percent, preferably at least 70 percent, most preferably at least 80 percent of the total weight of ethyl chloride produced in step (a) is subjected to cracking step (c).

In the ethyl chloride-rich fraction (II), the total amount of ethylene dichloride and vinyl chloride (which is often produced as a by-product in oxychlorination) is less than 30 percent, preferably less than 10 percent and more preferably less than 5 percent, based on the weight of ethyl chloride.

In general, the presence of ethylene dichloride or vinyl chloride decreases the lifetime of the catalyst in cracking step (c), however the presence of unreacted ethylene does not significantly affect the cracking step (c). For example, the ethyl chloride-rich fraction (II) may contain an ethyl chloride/ethylene molar ratio of 1:1 to 5:1 without significant impact on the cracking reaction. The ethyl chloride-rich fraction (II) is then fed to a cracking reactor.

It is preferred to carry out cracking step (c) in the presence of an inert diluent. It has been found that the lifetime of the catalyst and the conversion of ethyl chloride can be increased in the presence of an inert diluent such as nitrogen. The molar ratio between the inert diluent and ethyl chloride is preferably from 0.25:1, more preferably from 0.5:1, most preferably from 0.75:1, up to 30:1, preferably up to 20:1, more preferably up to 15:1. The combined amount of ethylene dichloride and vinyl chloride in the fraction (II) is less than 5 weight percent, preferably less than 4 weight percent and more preferably less than 3 weight percent, based on the combined weight of ethyl chloride and any inert diluent present in the fraction (II). If the combined amount of ethylene dichloride and vinyl chloride in fraction (II) is more than 5 percent of the ethyl chloride weight in fraction (II), a diluent has to be added.

The cracking reaction (c) is carried out at a suitable pressure and temperature. The cracking reaction (c) is generally carried out at a temperature between 150° C., preferably between 200° C., most preferably between 250° C., and 450° C., preferably 350° C., most preferably 320° C. The conversion of ethyl chloride increases with increasing temperature. Depending on the temperature in the reactor, a pressure preferably between 1 and 8 bar, more preferably between 1 and 5 bar, most preferably between 1 and 3 bar is maintained. The conversion of ethyl chloride to ethylene and hydrogen chloride increases with decreasing pressure, but vacuum operation is inconvenient in large scale cracking reactors.

The preferred residence time of ethyl chloride in the cracking reactor depends on several factors such as temperature and desired conversion rate. In general, a suitable residence time is from 2 sec., preferably from 3 sec., more preferably from 5 sec. and up to 120 sec., preferably up to 60 sec., more preferably up to 45 sec. Reasonable conversion rates are achievable at a residence time of 30 sec. or less.

Useful cracking catalysts for process step (c) are those which are generally known for cracking hydrocarbons, for example zeolite and silicalite catalysts. Preferred catalysts are aluminum oxide in various configurations, of which gamma-alumina is preferred. Gamma-alumina which has a surface area between 10 $m^2/g$, preferably between 50 $m^2/g$, more preferably between 100 $m^2/g$ and 350 $m^2/g$, preferably 320 $m^2/g$, more preferably 250 $m^2/g$ is preferred. It has been found that gamma-alumina which has a surface area between 50 $m^2/g$ and 250 $m^2/g$ and correspondingly a relatively large pore diameter, and which contains low levels of impurities such as $Na_2O$ and $SiO_2$, is relatively insensitive to reactant feed impurities such as ethylene dichloride and vinyl chloride. Only a few by-products are produced in the cracking reaction (c) when using these reaction catalysts. Preferably, the average pore diameter of the gamma-alumina is 3 to 30 nm, more preferably 6 to 20 nm. The level of impurities, such as $Na_2O$ and $SiO_2$, is preferably less than 15,000 ppm, more preferably less than 10,000 ppm, most preferably less than 1,000 ppm, based on the weight of gamma-alumina.

The effluent from the cracking reactor contains mainly ethylene and hydrogen chloride, inert diluent, if present, and minor amounts of impurities such as non-converted ethyl chloride. This effluent mixture can be treated as described below with reference to the drawing.

One preferred embodiment of the invention is explained in detail with reference to the drawing. In respect to said drawing, via lines 1, 2, 3 ethylene, hydrogen chloride and oxygen are fed to the oxychlorination reactor A in which ethylene is converted to 1,2-dichloroethane (ethylene dichloride) as described above (process step a). The temperature of ethylene, hydrogen chloride and oxygen to be fed is preferably from 180° to 400° C., more preferably from 200° to 380° C. The pressure in lines 1, 2 and 3 is preferably from 1 to 10 bar, more preferably from 2 to 8 bar. Nitrogen is generally used as an inert diluent for the reaction and is fed to the oxychlorination reactor A in the amount desired.

The effluent 4 from the oxychlorination reactor A is preferably cooled and excess hydrogen chloride is preferably removed from the effluent as described above with respect to the oxychlorination step (a). The effluent 4 then contains 1,2-dichloroethane and by-products.

The main by-product is ethyl chloride. Other by-products which are ordinarily found in effluent 4 are water, carbon dioxide, carbon monoxide and vinyl chloride. The effluent 4 further contains unreacted ethylene and any inert diluent. It may also contain trichloromethane and minor amounts of other impurities.

The effluent 4 from the oxychlorination reactor A is separated, preferably by condensation, into a gas fraction 6 and a liquid fraction 5. The fractionation (B1) is carried out in fractionation equipment B1, preferably in a condenser. The temperature in the fractionation equipment B1, in the gas fraction 6 and in the liquid fraction 5 is preferably from 20° C. to 120° C., more preferably from 30° C. to 100° C. The pressure in the fractionation equipment B1 is preferably from 1 bar to 10 bar, more preferably from 2 bar to 8 bar.

Gas fraction 6 contains mainly the inert diluent(s), carbon dioxide, carbon monoxide, non-converted ethylene and impurities. Preferably, gas fraction 6 is recycled to the oxychlorination reactor A.

The liquid fraction 5 consists mainly of 1,2-dichloroethane but also contains the major by-product ethyl chloride and minor amounts of other by-products such as vinyl chloride, water and/or trichloromethane, and of unconverted ethylene.

In a second fractionation equipment B2, liquid fraction 5 is separate in a fractionation step (b2) into a 1,2-dichloroethane fraction 8 and a by-product fraction 7, preferably by distillation. The temperature of the distillation is preferably from 30° C. to 180° C., more preferably from 40° C. to 140° C., and the distillation is preferably carried out at a pressure of from 1 bar to 10 bar, more preferably from 2 bar to 8 bar.

1,2-Dichloroethane fraction 8 contains crude 1,2-dichloroethane (ethylene dichloride) and can be further purified in a known manner. Fraction 8 has preferably a temperature of 30° C. to 150° C. and a pressure of 1 to 8 bar. The by-product fraction 7 contains mainly ethyl chloride and ethylene dichloride as well as by-products such as water, vinyl chloride and perhaps trichloromethane and non-converted ethylene. Fraction 7 preferably has a temperature of 20° C. to 100° C. and a pressure of 1 to 8 bar.

It is possible to feed by-product fraction 7 directly into the cracking reactor C in which ethyl chloride is converted into ethylene and hydrogen chloride as described above. In such a case, fraction 7 is preferably preheated to a temperature of from 150° C. to 450° C., more preferably of from 200° C. to 350° C. at a pressure of from 1 to 8 bar. However, it is preferred to subject fraction 7 to further fractionation steps in order to prolong the life of the catalyst in cracking step (c). It is evident that the usefulness of the fractionation steps (b3) and (b4) described below depends on the efficiency of the fractionation step (b2).

In fractionation step (b3) fraction 7 is further fractionated into a fraction 9 which contains at least the major portion of 1,2-dichloroethane and trichloromethane which might remain in fraction 7 after the fractionation step (b2) and into a fraction 10 which consists mainly of ethyl chloride and minor amounts of by-products ethylene, water and vinyl chloride.

The fractionation step (b3) in fractionation equipment (B3) is preferably carried out by distillation. The temperature of the distillation is preferably between 30° C. and 180° C., more preferably between 50° C. and 150° C. and the distillation is preferably carried out at a pressure between 1 bar and 10 bar, more preferably between 2 bar and 8 bar. Fraction 9 preferably has a temperature of 90° C. to 170° C., more preferably of 100° C. to 160° C. and a pressure of from 1 to 8 bar, preferably of 2 bar to 7 bar. Fraction 10 preferably has a temperature of 40° C. to 100° C., more preferably of 50° C. to 80° C. and preferably a pressure of 1 to 8 bar, more preferably of 1 bar to 7 bar.

Fraction 10 can be fed into cracking reactor C. In such a case fraction 10 is preferably preheated to a temperature of from 150° C. to 450° C., more preferably of from 200° C. to 350° C. at a pressure of from 1 to 8 bar. However, it is preferred to subject fraction 10 to a further fractionation step (b4) in the fractionation equipment B4 in order to avoid corrosion problems in the cracking reactor (C).

In fractionation equipment B4, fraction 10 is separated into a liquid water phase 11, a liquid ethyl chloride phase 12 and a gaseous ethyl chloride phase 13.

The pressure in fractionation equipment B4 is preferably from 1 to 8 bar, most preferably from 1 bar to 7 bar. The temperature is preferably from 20° C. to 100° C., more preferably from 30° C. to 90° C. The separation of the three phases is preferably carried out by means of gravity settling.

The liquid water phase 11 is removed from fractionation equipment B4. It preferably has a temperature of 20° C. to 100° C. and a pressure of 1 to 8 bar. The liquid ethyl chloride phase 12 which preferably has a temperature of 20° C. to 100° C. and a pressure of 1 to 8 bar, is sent to a vaporizer. This stream is combined with the gaseous ethyl chloride phase 13 from fractionation equipment B4. The gaseous ethyl chloride phase preferably has a temperature of 20° C. to 100° C. and a pressure of 1 to 8 bar. The combined ethyl chloride stream 14 consists mainly of ethyl chloride. The ethyl chloride stream 14 may also contain residual amounts of ethylene and vinyl chloride. The amount of vinyl chloride should not exceed the limit stated above.

It is to be understood that use of the fractionation steps (b1) to (b4) described with reference to the drawing is only one preferred embodiment of the fractionation step (b) of the effluent 4 from the oxychlorination reactor A. It is not critical how fractionation step (b) is carried out, however the ethyl chloride stream 14 should contain less than 30 weight percent ethylene dichloride and vinyl chloride (total amount), based on the weight of ethyl chloride.

The ethyl chloride stream 14 is then brought into the cracking reactor C. Preferably, it is diluted with an inert diluent 15 such as nitrogen. The ethyl chloride stream 14 and the inert diluent are preferably preheated to a temperature of from 150° C. to 450° C., more preferably of from 200° C. to 350° C. at a pressure of from 1 to 8 bar. The cracking reaction (c) is carried out as described above.

The effluent 16 from the cracking reactor C contains mainly ethylene, hydrogen chloride, inert diluent and minor amounts of by-products such as uncracked ethyl chloride. Hydrogen chloride is preferably separated from effluent 16, for example by adsorption of hydrogen chloride in washing equipment. Hydrogen chloride can be recovered as aqueous hydrochloric acid or it can be neutralised.

Preferably, effluent 16 from the cracking reactor C is then recycled to the oxychlorination step (a), most preferably after having separated unreacted ethyl chloride from effluent 16. Ethylene can be recycled to the oxychlorination step (a) or to another reaction in which ethylene is consumed, for example for producing ethylene dichloride via direct chlorination of ethylene, for example as described in U.S. Pat. No. 4,347,391.

The oxychlorination process described herein is preferably a continuous process.

The present invention is further explained in the following examples which illustrate the invention but are not intended to restrict it. All parts and percentages are by weight unless otherwise specified.

EXAMPLE 1

A gas stream consisting of 40.9 percent ethyl chloride, 16.6 percent ethylene, 1.9 percent vinyl chloride, 0.6 percent ethylene dichloride and 40 percent nitrogen is fed to a cracking reactor C. The gas stream corresponds to the combined streams 14 and 15 in the drawing. The gas stream is preheated to 250° C. The reactor is surrounded by a heat exchange jacket to maintain a temperature of 275° C. inside the reactor. The catalyst is gamma-alumina with a surface area of about 190 m$^2$/g and is arranged as a fixed bed. The pressure in the reactor is maintained at 1.8 to 2 bar. The average residence time of the flowing gas stream in the cracking reactor is 15 seconds.

Cracking reactor C is operated for about 100 days. The initial ethyl chloride conversion rate is 62.7%.

EXAMPLE 2

In order to evaluate the influence of vinyl chloride and ethylene dichloride on the catalyst used in cracking reaction (c) a gas steam consisting of 26.7 mol percent ethyl chloride, 24 mol percent ethylene, 47.2 mol percent nitrogen, 2.0 mol percent vinyl chloride and 0.1 mol percent ethylene dichloride is fed to the same cracking reactor C as in Example 1. The temperature, the residence time and the pressure are the same as in Example 1. Gamma-alumina having a surface area of about 200 m$^2$/g and a level of impurities (Na$_2$O and SiO$_2$) of less than 1,000 ppm is used as a catalyst. After having operated the cracking reactor for about 100 days, the ethyl chloride conversion rate is reduced to about 50 percent of its initial rate.

EXAMPLE 3

Example 2 is repeated, however gamma-alumina having a surface area of about 300 m$^2$/g and a level of impurities (Na$_2$O and SiO$_2$) of about 10,000 ppm is used as a catalyst. After having operated the cracking reactor for about 25 days, the ethyl chloride conversion rate is reduced to about 65 percent of its initial rate.

EXAMPLE 4

Example 3 is repeated, however the gas feed stream consists of 27.2 mol percent ethyl chloride, 24.5 mol percent ethylene and 48.3 mol percent nitrogen. After 50 days, the ethyl chloride conversion rate is reduced to about 65 percent of its initial rate.

EXAMPLE 5

Example 2 is repeated, however the average residence time of the flowing gas stream in the cracking reactor is 30 seconds. After having operated the cracking reactor for about 100 days, the ethyl chloride conversion rate is reduced to about 70 percent of its initial rate.

EXAMPLES 6 to 21

To evaluate the influence of the temperature, the pressure and the residence time on the ethyl chloride conversion rate, a gas stream consisting of about 27 mol percent ethyl chloride (EtCl), about 24 mol percent ethylene (C$_2$H$_4$) and about 49 mol percent nitrogen (N$_2$) is heated to 250° C. This stream simulates a stream obtained in the oxychlorination step (a) and in fractionating step (b). The cracking reaction (c) takes place in a reactor into which the gas stream is continuously fed.

The results are set forth in Table I.

TABLE I

| Example | T (°C.) | Pressure (bar) | Residence time (seconds) | Feed (molar ratios) C$_2$H$_4$ | Feed (molar ratios) EtCl | Feed (molar ratios) N$_2$ | Products (molar ratios) C$_2$H$_4$ | Products (molar ratios) EtCl | Products (molar ratios) N$_2$ | Ethyl chloride conversion rate (%) |
|---|---|---|---|---|---|---|---|---|---|---|
| 6 | 262 | 1 | 5 | 1.68 | 1.87 | 3.45 | 1.83 | 1.23 | 3.45 | 34.1 |
| 7 | 262 | 1 | 10 | 1.19 | 1.32 | 2.44 | 1.84 | 0.66 | 2.44 | 50.3 |
| 8 | 262 | 1 | 15 | 0.59 | 0.66 | 1.29 | 1.07 | 0.23 | 1.29 | 65.9 |
| 9 | 273 | 1 | 5 | 1.68 | 1.87 | 3.45 | 2.17 | 1.04 | 3.45 | 38.1 |
| 10 | 273 | 1 | 10 | 1.17 | 1.30 | 2.39 | 1.89 | 0.56 | 2.39 | 57.1 |
| 11 | 273 | 1 | 15 | 0.39 | 0.43 | 0.80 | 0.77 | 0.14 | 0.80 | 68.1 |
| 12 | 282 | 1 | 5 | 1.68 | 1.87 | 3.45 | 2.39 | 0.88 | 3.45 | 52.9 |
| 13 | 282 | 1 | 10 | 1.42 | 1.58 | 2.92 | 2.63 | 0.61 | 2.92 | 61.4 |
| 14 | 282 | 1 | 15 | 0.62 | 0.59 | 1.23 | 1.09 | 0.17 | 1.23 | 76.0 |
| 15 | 290 | 1 | 5 | 1.11 | 1.25 | 2.30 | 1.98 | 0.32 | 2.30 | 74.0 |
| 16 | 290 | 1 | 10 | 0.56 | 0.62 | 1.14 | 1.14 | 0.12 | 1.14 | 80.1 |
| 17 | 290 | 1 | 15 | 0.37 | 0.41 | 0.76 | 0.72 | 0.07 | 0.76 | 82.7 |
| 18 | 282 | 2 | 15 | 0.71 | 0.79 | 1.46 | 1.23 | 0.32 | 1.46 | 60.0 |
| 19 | 282 | 3 | 15 | 1.16 | 1.28 | 2.38 | 1.57 | 0.52 | 2.38 | 58.2 |
| 20 | 282 | 4 | 15 | 1.23 | 1.36 | 2.52 | 1.79 | 0.65 | 2.52 | 52.7 |
| 21 | 282 | 5 | 15 | 1.53 | 1.71 | 3.15 | 2.19 | 0.95 | 3.15 | 44.6 |

What is claimed is:

1. An oxychlorination process for producing ethylene dichloride by
   (a) reacting ethylene with hydrogen chloride and oxygen in the presence of an oxychlorination catalyst in an oxychlorination reactor, whereby ethyl chloride or both ethyl chloride and vinyl chloride are produced as by-products which process comprises the further steps of
   (b) dividing, in one or more steps, the effluent from the oxychlorination reactor into at least (i) an ethylene dichloride-rich fraction (I) and (ii) an ethyl chloride-rich fraction (II) in such a fashion that fraction (I) contains less than about 50 percent of the total weight of ethyl chloride produced in step (a) and the sum of the weight of ethylene dichloride and vinyl chloride in fraction (II) is less than about 30 percent of the weight of ethyl chloride in fraction (II) and
   (c) subjecting fraction (II) to a cracking process in the presence or absence of an inert diluent whereby fraction (II) contains less than about 5 percent ethylene dichloride and vinyl chloride, based on the combined weight of ethyl chloride and inert diluent in fraction (II) prior to cracking, the cracking process being carried out in the presence of a cracking catalyst in a cracking reactor wherein ethyl chloride is converted into ethylene and hydrogen chloride.

2. The process of claim 1 wherein step (c) is carried out at a temperature between about 250° C. and about 320° C.

3. The process of claim 1 wherein step (c) is carried out at a pressure between about 1 and about 8 bar.

4. The process of claim 1 wherein the residence time of ethyl chloride in the cracking reactor is from about 5 to about 60 seconds.

5. The process of claim 1 wherein step (c) is carried out in the presence of nitrogen.

6. The process of claim 1 wherein the ethyl chloride-rich fraction (II) is once or twice distilled at a temperature between about 30° C. and about 180° C. at a pressure between about 1 and about 10 bar before carrying out step (c).

7. The process of claim 1 wherein water is removed from the ethyl chloride-rich fraction (II) before carrying out step (c).

8. The process of claim 1 wherein ethylene obtained in step (c) is recycled to process step (a).

9. The process of claim 1 wherein the cracking catalyst used in step (c) is aluminum oxide.

10. The process of claim 9 wherein the catalyst is gamma-alumina having a surface area between about 10 m$^2$/g and about 350 m$^2$/g.

11. The process of claim 10 wherein the catalyst is gamma-alumina having a surface area between about 50 m$^2$/g and about 250 m$^2$/g.

12. The process of claim 10 wherein step (c) is carried out in the presence of nitrogen.

13. The process of claim 10 wherein the ethyl chloride-rich fraction (II) is once or twice distilled at a temperature between about 30° C. and about 180° C. at a pressure between about 1 and about 10 bar before carrying out step (c).

14. The process of claim 10 wherein water is removed from the ethyl chloride-rich fraction (II) before carrying out step (c).

15. The process of claim 10 wherein ethylene obtained in step (c) is recycled to process step (a).

16. The process of claim 1 wherein step (c) is carried out at a temperature between about 250° C. and about 320° C., at a pressure between about 1 and about 8 bar and in the presence of nitrogen, the residence time of ethyl chloride in the cracking reactor is from about 5 to about 60 seconds and the cracking catalyst used in step (c) is aluminum oxide.

17. The process of claim 16 wherein the catalyst is gamma-alumina having a surface are between about 10 m$^2$/g and about 350 m$^2$/g.

18. The process of claim 17 wherein the catalyst is gamma-alumnia having a surface area between about 50 m$^2$/g and about 250 m$^2$/g.

19. The process of claim 18 wherein the ethyl chloride-rich fraction (II) is once or twice distilled at a temperature between about 30° C. and about 180° C. at a pressure between about 1 and about 10 bar before carrying out step (c).

20. The process of claim 18 wherein water is removed from the ethyl chloride-rich fraction (II) before carrying out step (c).

* * * * *